(12) United States Patent
Lo et al.

(10) Patent No.: US 10,500,085 B2
(45) Date of Patent: Dec. 10, 2019

(54) BED SET FOR INHIBITION OBSTRUCTIVE SLEEP APNEA

(71) Applicant: National Central University, Taoyuan (TW)

(72) Inventors: Men-Tzung Lo, Taoyuan (TW); Leh-Kiong Huon, Sarawak (MY); Van-Truong Pham, Hai Phong (VN); Yunn-Jy Chen, Taipei (TW); Ting-Fang Shih, Taipei (TW); Thi-Thao Tran, Vinh Phuc Province (VN); Chen Lin, Taoyuan (TW); Pa-Chun Wang, Taipei (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 581 days.

(21) Appl. No.: 15/293,632

(22) Filed: Oct. 14, 2016

(65) Prior Publication Data

US 2017/0319376 A1 Nov. 9, 2017

(30) Foreign Application Priority Data

May 5, 2016 (TW) .............................. 105113963 A (51) Int. Cl.
*A61F 5/56* (2006.01)
*A61B 5/00* (2006.01)
*A61B 5/087* (2006.01)

(52) U.S. Cl.
CPC ................ *A61F 5/56* (2013.01); *A61B 5/002* (2013.01); *A61B 5/087* (2013.01); *A61B 5/4818* (2013.01); *A61B 5/7405* (2013.01)

(58) Field of Classification Search
CPC ........... A61F 5/56; A61B 5/002; A61B 5/087; A61B 5/0873; A61B 5/4818;
(Continued)

(56) References Cited

U.S. PATENT DOCUMENTS 4,941,478 A * 7/1990 Takeuchi .................. A61F 5/56
128/848
8,347,434 B2 * 1/2013 Chan .................... A47G 9/1027
5/636

(Continued)

*Primary Examiner* — Jason R Kurr
(74) *Attorney, Agent, or Firm* — Muncy, Geissler, Olds & Lowe, P.C.

(57) ABSTRACT

The present invention provides a bed set for inhibition of obstructive sleep apnea, which includes: a sound receiving module, is used to receive a respiratory sound signal obtained from a user during a time period; a sound analyzing processor, which is connected with the sound receiving module, is used to obtain a snoring sound characteristic from the spectrum of respiratory sound signal; a database, which has a plurality of snoring image characteristics corresponding to a plurality of basic snoring sound characteristics for different respiratory actions; a control processor, which is connected with the sound analyzing processor and the database, is used to compare the snoring sound characteristic with the basic snoring sound characteristics to select one of the snoring image characteristics in the same waveform, and provides the first angle control order and the second angle control order corresponding to the selecting snoring image characteristic; a first pillow, which is connected to the control processor, declines a first angle toward a declination direction after receiving the first control order; and a second pillow, which is connected to the control processor, declines a second angle toward the declination direction after receiving the second control order.

13 Claims, 8 Drawing Sheets

(58) Field of Classification Search
CPC ... A61B 5/7405; A61B 5/4806; A61B 5/4815; H04R 29/00; H04R 29/008; H04R 29/004; A47C 20/04; A47C 20/041; A47C 20/08; A47G 9/1027; A47G 9/109; A47G 2200/146
See application file for complete search history.

(56) References Cited

U.S. PATENT DOCUMENTS

| | | | |
|---|---|---|---|
| 10,105,092 B2* | 10/2018 | Franceschetti | A61B 5/4836 |
| 2008/0052837 A1* | 3/2008 | Blumberg | A47C 23/002 |
| | | | 5/727 |
| 2012/0324649 A1* | 12/2012 | Lin | A61B 5/0002 |
| | | | 5/613 |
| 2014/0245539 A1* | 9/2014 | Ooba | A47C 20/048 |
| | | | 5/636 |
| 2014/0259417 A1* | 9/2014 | Nunn | A61G 7/015 |
| | | | 5/614 |
| 2015/0335507 A1* | 11/2015 | Emmons | G16H 20/00 |
| | | | 5/615 |
| 2016/0007914 A1* | 1/2016 | Xu | A61B 5/4815 |
| | | | 600/301 |
| 2016/0120716 A1* | 5/2016 | Ribble | A61B 5/6892 |
| | | | 5/616 |
| 2016/0286974 A1* | 10/2016 | Boyd | A47C 20/041 |
| 2017/0238736 A1* | 8/2017 | Ho | A47G 9/1027 |
| 2019/0099009 A1* | 4/2019 | Connor | A47C 27/083 |

* cited by examiner

BED SET FOR INHIBITION OBSTRUCTIVE SLEEP APNEA

CROSS-REFERENCE TO RELATED APPLICATIONS

This Non-provisional application claims priority under 35 U.S.C. § 119(a) on Patent Application No(s). [105113963] filed in Taiwan, Republic of China [May 5, 2016], the entire contents of which are hereby incorporated by reference.

FIELD OF THE INVENTION

The present invention provides a bed set for inhibition of obstructive sleep apnea, by declining pillows in the different angles respectively assisting the user's body to achieve the goal of normal breathing.

BACKGROUND OF THE INVENTION

Sleep apnea is one kind of sleep disorder. The male, the obesity, the alcoholism and those who reply on sleeping pills and sedatives have greater chance to contract the sleep apnea, wherein elderly patients' percentage is even higher than younger patients'. Sleep apnea patients often wake up during sleep due to breathing obstacles, and are able to return normal breath after waking up, then soon to back to sleep. However, the breathing obstacles may happen more than hundreds of times during a night, and the duration of time period would vary from second to more than one minute. Because of above reason, the patients usually have poor sleep quality, thereby decrease the effectiveness of work or daily life.

Sleep apnea can be classified as three categories: (1) obstructive sleep apnea (Obstructive Sleep Apnea, OSA), which is the most common one, has about 90% of patients belong to this category. The cause of OSA is the physiological obstruction being close to the soft tissue of throat airway, so that the upper airway will become narrow, and lead to have snoring and apnea. Upper respiratory tract structural abnormalities (e.g. bent nasal septum, turbinate hypertrophy, nasal polyps, hyperplasia, long uvula, adenoids, tongue hypertrophy, etc.), excessive airway muscle relaxation and obesity are also a cause of OSA. (2) Central sleep apnea (Central Sleep Apnea, CSA) is a kind of sleep apnea caused by brain stroke, traumatic impact or other problems; the brain of patient cannot issue instructions and lead to breathing sleep apnea. Another problem is the occurrence of central nervous system that respiratory message instruction conduction being abnormalities, so that the respiratory movements will have problem and stop breathing. (3) Mixed sleep apnea (Mixed Apnea) is a patient suffering both of obstructive and central sleep apnea.

One of current methods for preventing sleep apnea disease is treatment by surgery. However, because of the physiological structure of upper airway is complex, not every patient is suitable for surgery. In the common method, medical staff will suggest patient to have positional sleeping and reduce the intake of alcohol or sleeping pills for sleep apnea. It is difficult for patients to maintain the posture for whole night, so that the patients often rely on positional pillow to maintain the posture. There are some available pillows claiming for inhibiting sleep snoring, but those pillows are often designed to change the position of the user's head through height adjustment. However, the medical "sleep snoring", especially refer to OSA, cannot be overcome only by changing the vertical position of user's head; therefore, the traditional methods are still unable to solve the problem of snoring sleep effectively.

SUMMARY OF THE INVENTION

For above reason, the present invention provides a bed set for inhibiting the each king of sleep apnea, which is associated with a database to determine the location of the sleep apnea and airway collapse situation, further decline the head and body with different angles respectively according to a user's body axis, to achieve the posture of back to normal breathing; and then repeat the signal to confirm the user's breathing, if the breathing has returned to normal signal, the bed set would decline to the opposite direction of the original direction to make the user return to the initial sleep situation.

Thus, the design of bed set comprises: a sound receiving module, is used to receive a respiratory sound signal obtained from a user during a time period; a sound analyzing processor, which is connected with the sound receiving module, is used to obtain a snoring sound characteristic from the spectrum of respiratory sound signal; a database, which has a plurality of snoring image characteristics corresponding to a plurality of basic snoring sound characteristics for different respiratory actions, wherein each of the snoring image characteristic binds with a first angle control order and a second angle control order; a control processor, which is connected with the sound analyzing processor and the database, is used to compare the snoring sound characteristic with the basic snoring sound characteristics to select one of the snoring image characteristics in the same waveform, and provides the first angle control order and the second angle control order corresponding to the selecting snoring image characteristic; a first pillow, which is connected to the control processor, is a first declining module wrapped by a soft material, wherein the first pillow is putted under the user's head while using and declines a first angle toward a declination direction after receiving the first control order; and a second pillow, which is connected to the control processor, is a second declining module wrapped by the soft material, wherein the second pillow is putted under the user's body and neck while using and declines a second angle toward the declination direction after receiving the second control order.

Preferably, the time period is a soft tissue vibration duration obtained from the user's respiratory tract during a respiratory action.

Preferably, the sound receiving module further filters the noise of respiratory sound signal by Principal Component Analysis (PCA).

Preferably, the respiratory sound signal is a spectrum harmonic wave obtained by short-time Fourier transforming with Gauss window function from the respiratory sound signal during a respiratory action.

The design of bed set further comprises: an image receiving module, is used to receive a plurality of respiratory image signals obtained from the user during the time period; an image analyzing processor, which is connected to the image receiving module, is used to obtain a snoring image characteristic calculated from the respiratory image signals base on the same region of the respiratory tract and an interesting area; the control processor, which is further connected to the image processing processor, is used to compare the snoring sound characteristic with the basic snoring sound characteristics and compare the snoring image characteristic with the basic snoring image characteristics to select one of the snoring image characteristic in the same waveform and provides the first angle control order and the second angle control order corresponding to the selecting snoring image characteristic; wherein the snoring image characteristic is classified according to the basic snoring sound characteristics and a plurality of basic snoring image characteristics in different respiratory actions.

Preferably, the image receiving module further uses an adaptive partial averaging filter to enhance the noise ratio of respiratory image signal.

Preferably, the respiratory image signal is a side view.

Preferably, the snoring image characteristic is the region ratio of the respiratory tract and the interested area during a respiratory action.

Preferably, the respiratory area is obtained from the interested area divided by the Active Contour Model (ACM).

Preferably, the control processor further obtains a time reference according to the receiving sequence of respiratory image signals, and corrects the time error between snoring sound characteristic and snoring image characteristic base on the time reference.

Preferably, the first pillow and the second pillow incline the first angle and the second angle in the same direction, and the rotating axis of first pillow and second pillow is parallel to the user's body.

Preferably, the first angle and second angel are respectively one of 15 degrees, 30 degrees and 60 degrees.

Preferably, the first pillow and the second pillow are the part of a L-shaped pillow.

DETAILED DESCRIPTION OF THE INVENTION

For the examiners and the skilled persons in the art be clear to understand the present invention, the following information will show the implement of present invention through figures and illustrations.

Figure 1:
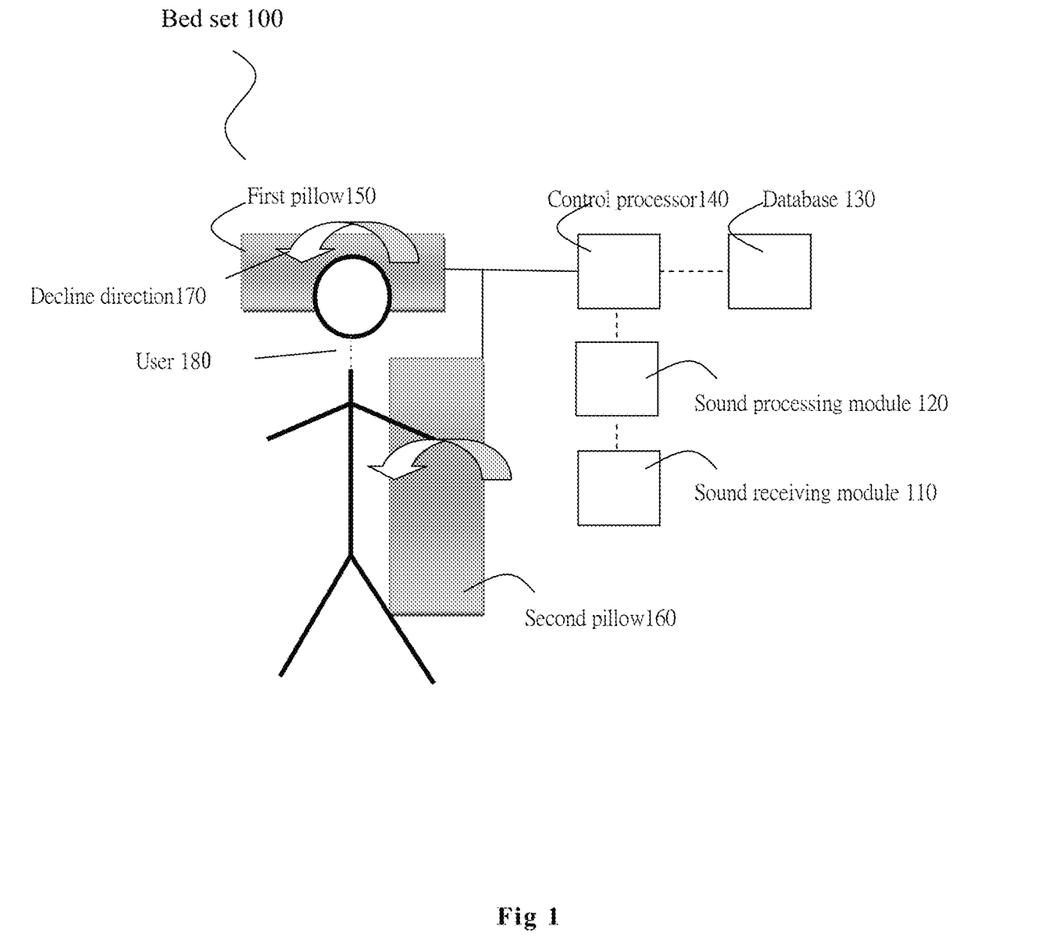
FIG. 1 is the illustrative figure of one embodiment of the bed set for inhibition the obstructive sleep apnea in the present invention.

As shown in FIG. 1, the present invention provides a bed set for inhibition of obstructive sleep apnea 100, which includes: a sound receiving module 110, is used to receive a respiratory sound signal obtained from a user 180 during a time period; a sound analyzing processor 120, which is connected with the sound receiving module 110, is used to obtain a snoring sound characteristic from the spectrum of respiratory sound signal; a database 130, which has a plurality of snoring image characteristics corresponding to a plurality of basic snoring sound characteristics for different respiratory actions, wherein each of the snoring image characteristic binds with a first angle control order and a second angle control order; a control processor 140, which is connected with the sound analyzing processor and the database, is used to compare the snoring sound characteristic with the basic snoring sound characteristics to select one of the snoring image characteristics in the same waveform, and provides the first angle control order and the second angle control order corresponding to the selecting snoring image characteristic; a first pillow 150, which is connected to the control processor, is a first declining module wrapped by a soft material, wherein the first pillow 150 is putted under the user's head while using and declines a first angle toward a declination direction after receiving the first control order; and a second pillow 160, which is connected to the control processor, is a second declining module wrapped by the soft material, wherein the second pillow 160 is putted under the user's body and neck 180 while using and declines a second angle toward the declination direction after receiving the second control order.

Preferably, the bed set 100 further comprises: an image receiving module, is used to receive a plurality of respiratory image signals obtained from the user during the time period; an image analyzing processor, which is connected to the image receiving module, is used to obtain a snoring image characteristic calculated from the respiratory image signals base on the same region of the respiratory tract and an interesting area; the control processor, which is further connected to the image processing processor, is used to compare the snoring sound characteristic with the basic snoring sound characteristics and compare the snoring image characteristic with the basic snoring image characteristics to select one of the snoring image characteristic in the same waveform, and provides the first angle control order and the second angle control order corresponding to the selecting snoring image characteristic; wherein the snoring image characteristic is classified according to the basic snoring sound characteristics and a plurality of basic snoring image characteristics in different respiratory actions.

In one embodiment of the present invention, the image receiving module further uses an adaptive partial averaging filter to enhance the noise ratio of the respiratory image signals.

In one embodiment of the present invention, the respiratory image signal is a sagittal view.

In one embodiment of the present invention, the snoring image characteristic is the region ratio of respiratory tract and the interested area during a respiratory action.

In one embodiment of the present invention, the respiratory area is obtained from the interested area by the Active Contour Model (ACM).

In one embodiment of the present invention, the control processor further obtains a time reference according to the order of receiving the respiratory image signal, and corrects the time error between snoring signal characteristics and the snoring image characteristic base on the time reference.

Figure 2:
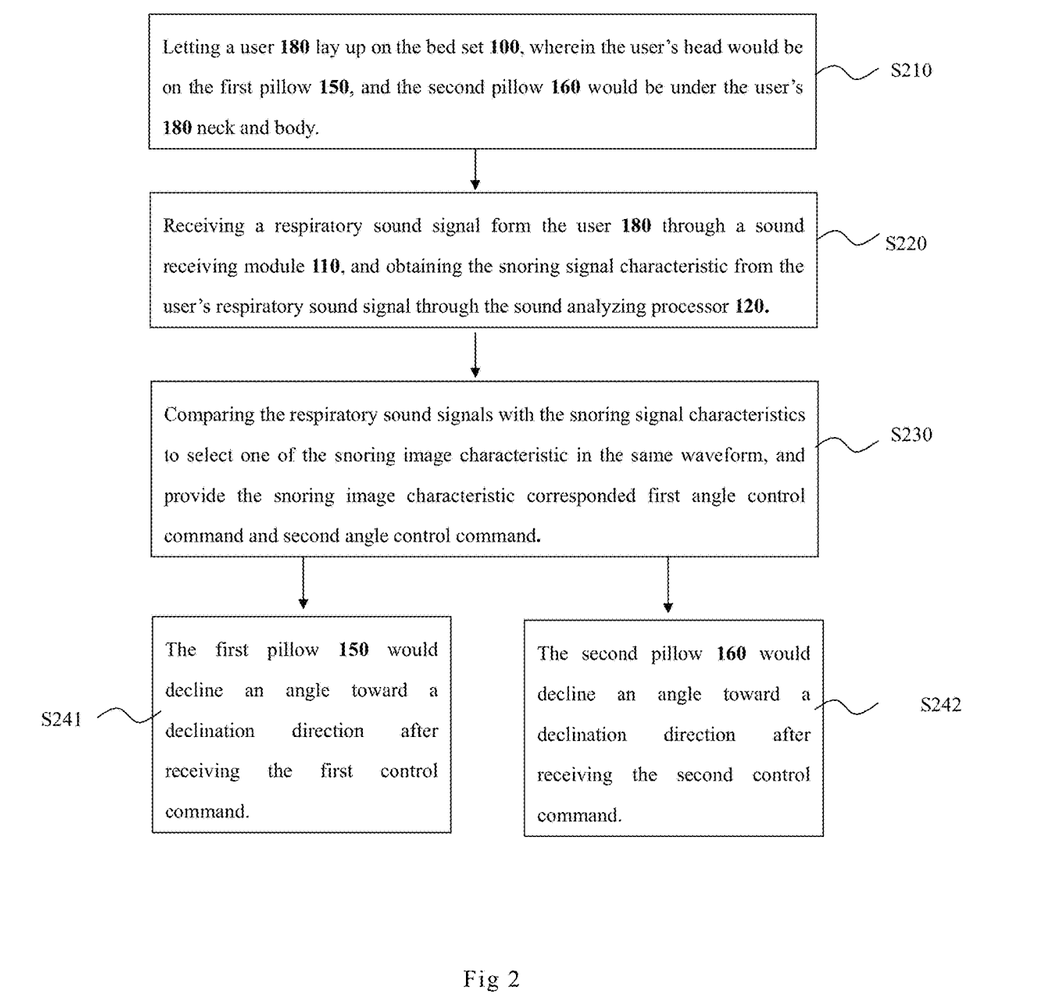
FIG. 2 is the flow chart of one embodiment method for preventing the obstructive sleep apnea in the present invention.

As shown in FIG. 2, the present invention provides a method for preventing obstructive sleep apnea through the bed set of the present invention 100, which comprises the following steps: letting a user 180 lay up on the bed set 100, wherein the user's head would be on the first pillow 150, and the second pillow 160 would be under the user's 180 neck and body, S210; receiving a respiratory sound signal form the user 180 through the sound receiving module 110, and obtaining the snoring signal characteristic from a user's respiratory signals through the sound analyzing processor 120, S220; comparing the respiratory sound signals with the snoring signal characteristic to selected one of the snoring image characteristic in the same waveform, and provide the snoring image characteristic corresponded first angle control command and second angle control command, S230; the first pillow 150 would decline an angle toward a declination direction after receiving the first control command, S241; and the second pillow 160, Would decline an angle toward a declination direction after receiving the second control command, S242.

Figure 3:
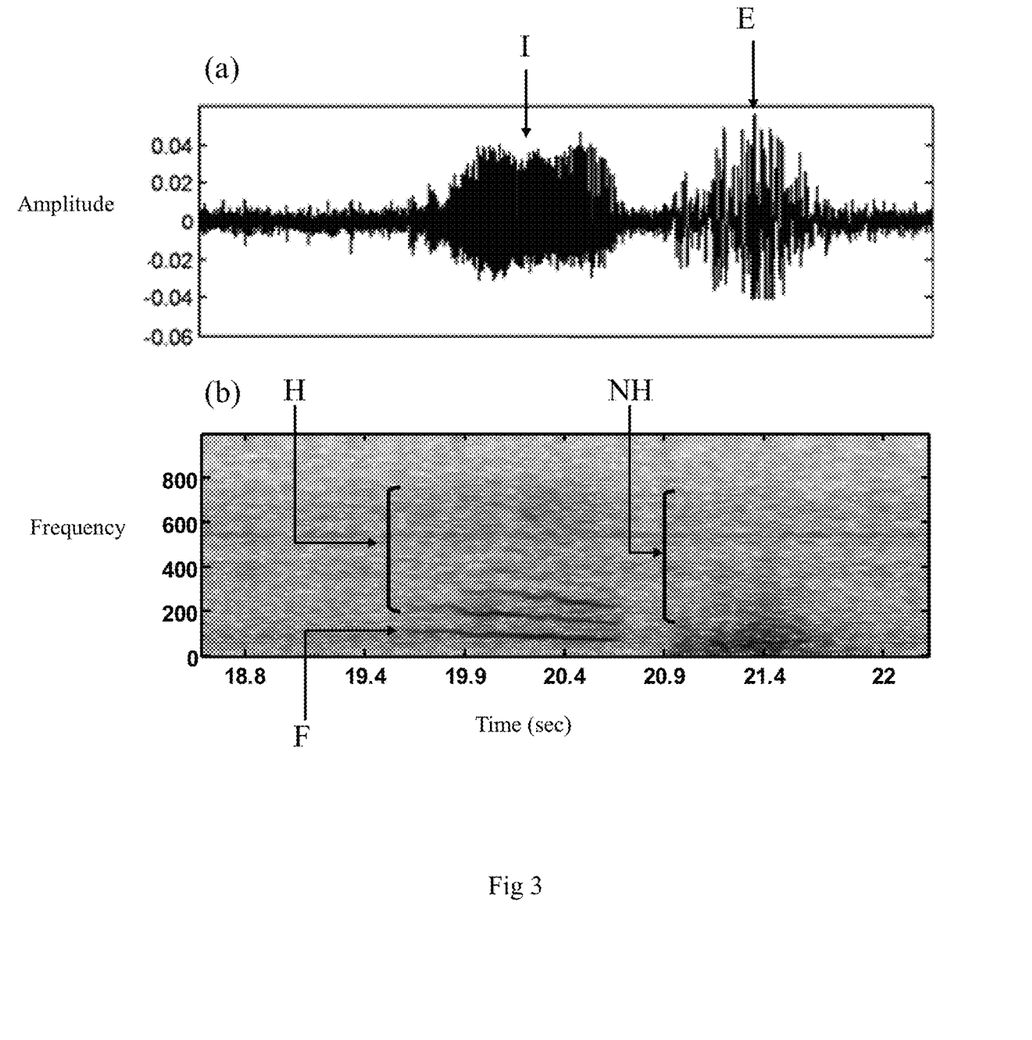
FIG. 3 shows the snoring signals of inhalation I and exhalation E, and the spectrums thereof in the present invention.

As shown in FIG. 3, there are several different waveforms in FIG. 3(*a*), which is the de-noised snoring signals, and the inhalation I and exhalation E could be distinguished. The snoring signal characteristic is transformed by short-time Fourier and acquired by Gauss window function, to obtain the respiratory sound signals as FIG. 3(*b*), wherein the window of Gauss is 0.1 seconds, and the displacement between two successive windows is 0.005 seconds. The harmonic waves H, the foundation waves F, and the non-harmonic waves NH can be seen in fig (b).

According to the inventors' observation, the subject's muscle tension would reduce so that he/she would be unable to support the upper respiratory tract tissue structures. The air would flow through the soft tissues of the upper respiratory tract and soft tissue vibrations would generate harmonic wave (H) and generating snoring at the same time during inhalation, and the non-harmonic waves (NH Part) would not occur while exhalation. Thus, we could obtain the data of inspiratory and expiratory time frame and the snoring duration from the snoring signals spectrogram. Thus, the snoring signal characteristics can be obtained by the harmonic waves of the spectrum. Harmonic wave duration is equal to the duration of soft tissue vibration, and it can be regarded as the snoring signal characteristics.

Figure 4:
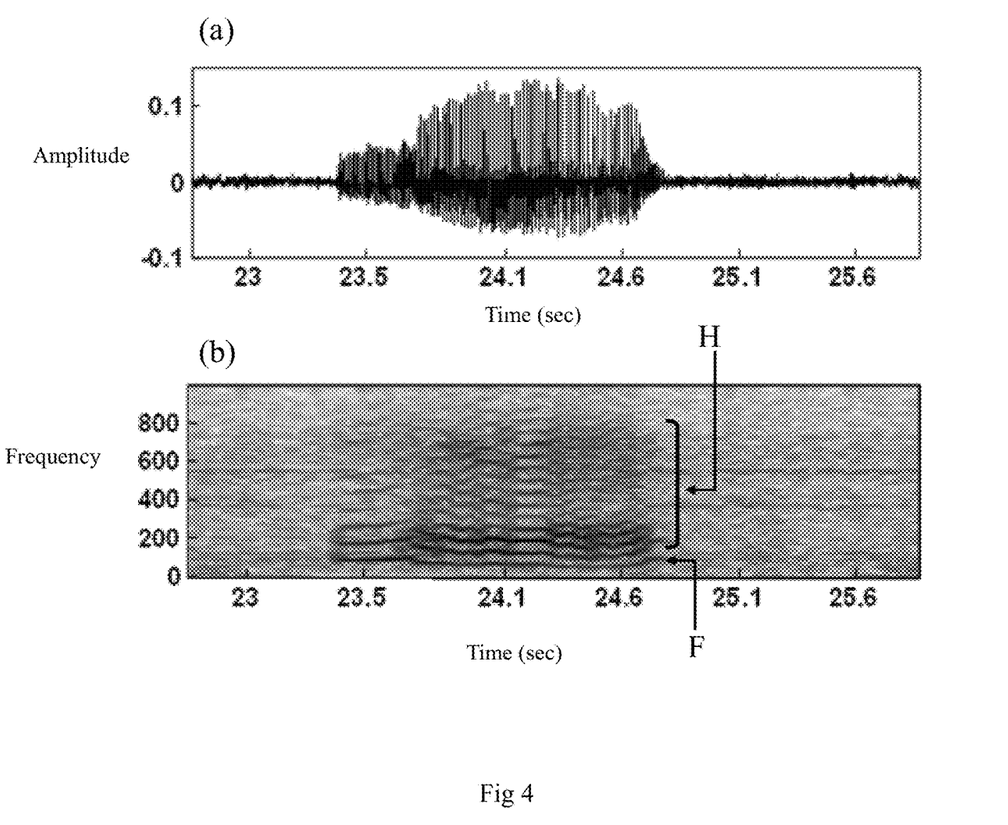
FIG. 4 shows the snoring signals of one embodiment, and the spectrums thereof in the present invention.
Figure 5:
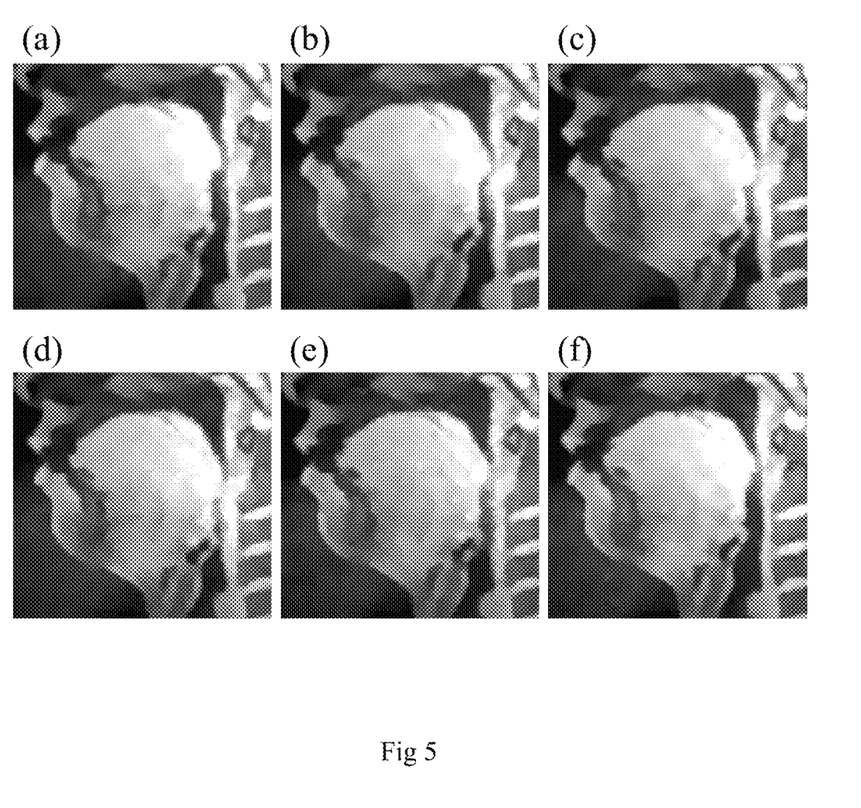
FIG. 5 shows the respiratory motion pictures and the airway collapse indexes corresponded to the snoring signals of FIG. 4.

As shown in FIGS. 4 and 5, there is a snoring signal in FIG. 4(*a*), and the spectrum is in FIG. 4(*b*) which shows the harmonic waves. The duration of soft tissue vibration is equal to the harmonic wave duration, during this time period, the snoring occurs simultaneously. H represents the harmonic waves, F represents the foundation waves, and NH represents the non-harmonic waves.

Comparing the data in FIGS. 5(*a*) to 5(*f*) diagram, the time duration of FIG. 5(*a*) is 23.0 seconds; the snoring image characteristic was 15.8%, and the time duration of FIG. 5(*b*) of 23.5 seconds, snoring image characteristic was 9.8%; the time duration of FIG. 5(*c*) is 24.1 seconds, snoring image characteristic was 6.8%; the time duration of FIG. 5(*d*) is 24.6 seconds, snoring image characteristic was 5.4%; the time duration of FIG. 5(*e*) is 25.1 seconds, snoring image characteristic was 10.3%; the time duration of FIG. 5(*f*) is 25.6 seconds, snoring image characteristic was 16.4%. The tongue area gradually collapse is observed in FIG. 5(*a*) through FIG. 5(*c*), the snoring sound is found in FIG. 4, and reach to the end in FIG. 5 (*d*) wherein the inspiratory snoring image characteristic decrease to the minimum, and the snoring sound ends. Then, the collapsed airways expand again in FIGS. 5(*d*) to 5(*f*) and there is no harmonic wave in the spectrogram due to the end of snoring sound.

Figure 6:
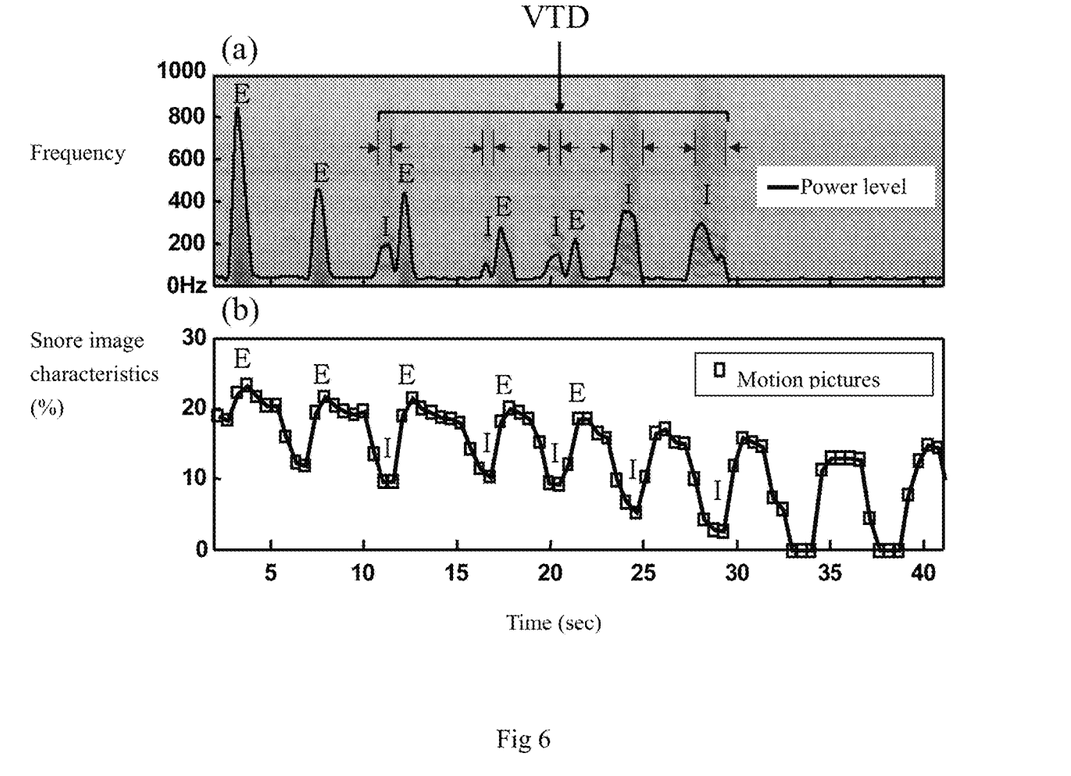
FIG. 6 shows the continuous snoring sound signal spectrums of one embodiment, and the graph of airway collapse indexes thereof in the present invention.

As shown in FIG. 6(*a*), the inhalation I and exhalation E can be distinguished, and the harmonic waves are also identifiable; and the 5 soft tissue vibration time durations VTD are snoring sound signals can also be defined after converting the continuous breathing sound signal to spectrums. FIG. 6(*b*) shows the graph of calculation result of snoring image characteristic from recorded the respiratory sound signals and motion pictures continuously at the same time, wherein the sampling frequency is 0.5 Hz. The gradually collapsed airway (snoring image characteristic is decreasing) is observed from the vibration duration of 5 soft tissues, the corresponding motion pictures, and the snoring image characteristics. There are two serious snore events during 25 s and 30 s, which is observed in tongue and soft palate obstruction, meanwhile, the snoring image characteristic has been below 10%, and the soft tissue vibrates a longer duration. During 30 s to 40 s, the collapse of the rear tongue area has been completely blocked, this time to stop snoring.

Figure 7:
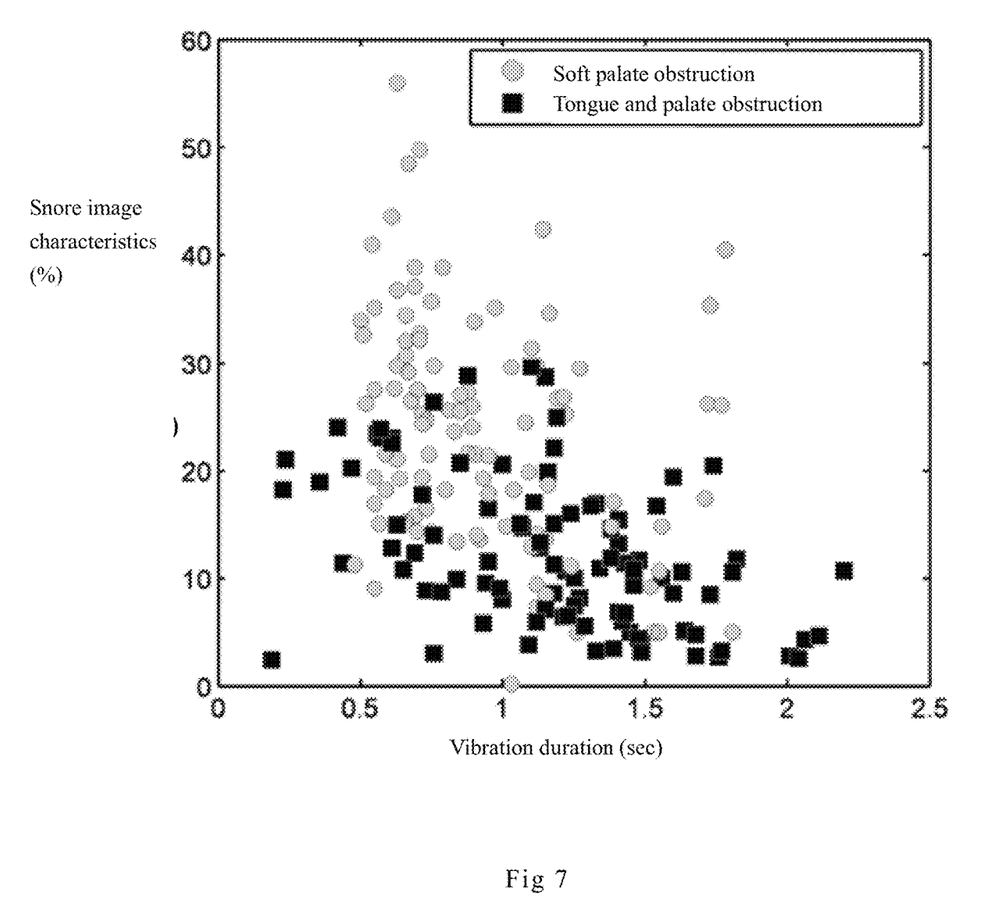
FIG. 7 shows the association figure of airway collapse indexes of one embodiment, and the snoring signal characteristics with different obstruction areas thereof in the present invention.
Figure 8:
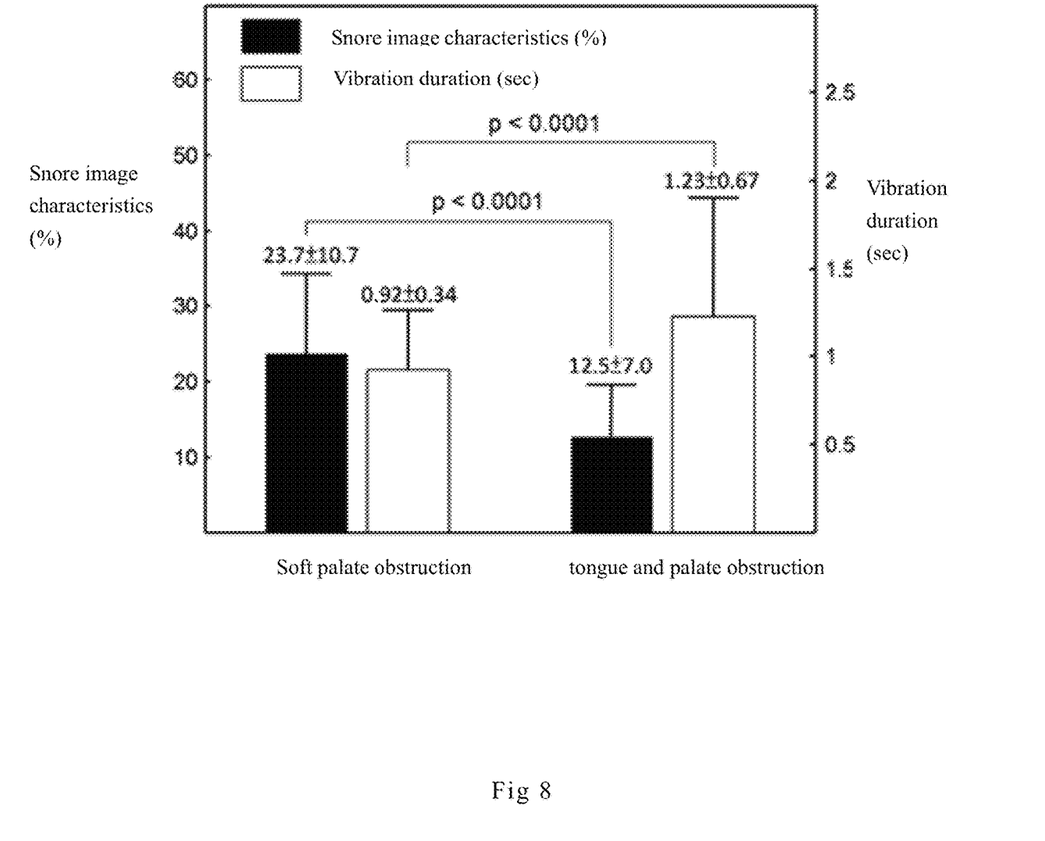
FIG. 8 shows the statistic chart of airway collapse indexes of one embodiment, and snoring signal characteristics with different obstruction areas thereof in the present invention.

FIG. 7 shows the correlation graph of the associated database information, wherein the different blocking positions have different airway collapse indexes and vibration durations. FIG. 8 shows the statistic chart of snoring image characteristic, wherein the vibration durations are significantly different due to the different blocking position and different value segments, wherein snoring image characteristics are associated with the vibration durations. As shown in the chart, the different blocking position of different sleep apneas shows significant different snoring image characteristic statistically; for example, the airway collapse index is about 24%±11% in soft palate obstruction, and the airway collapse index is about 13%±7%[$P \leq 0.0001$] in tongue and soft palate obstruction. Thus, the associated database information can be used for calculating the vibration duration associated snoring image characteristic, so as to identify the airway collapse position of sleep apnea.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A bed set for inhibition of obstructive sleep apnea, which includes:
   a sound receiver, configured to receive a respiratory sound signal obtained from a user during a time period;
   a sound analyzing processor, which is connected with the sound receiver, which is used to obtain a snoring sound characteristic from the respiratory sound signal;
   a database, which has a plurality of snoring image characteristics corresponding to a plurality of basic snoring sound characteristics for different respiratory actions, wherein each of the snoring image characteristics binds with a first angle control order and a second angle control order;
   a control processor, which is connected with the sound analyzing processor and the database, which is used to compare the snoring sound characteristic with the basic snoring sound characteristics to select one of the snoring image characteristic in a same waveform, and provides the first angle control order and the second angle control order corresponding to the selected snoring image characteristic;
   a first pillow, which is connected to the control processor, is a first declining module wrapped by a soft material, wherein the first pillow is placed under the head of the user while using and declines a first angle toward a declination direction after receiving the first control order; and a second pillow, which is connected to the control processor, is a second declining module wrapped by the soft material, wherein the second pillow is placed under the body and neck of the user while using and declines a second angle toward the declination direction after receiving the second control order.

2. The bed set of claim 1, wherein the time period is a soft tissue vibration duration obtained from the user's respiratory tract during a respiratory action.

3. The bed set of claim 2, which further comprises:

an image receiver, configured to receive a plurality of respiratory image signals obtained from the user during the time period; and an image analyzing processor, which is connected to the image receiver, which is used to obtain a snoring image characteristic calculated from the respiratory image signals based on a same region of the respiratory tract and an interesting area;

the control processor, which is further connected to an image processing processor, which is used to compare the snoring sound characteristic with the basic snoring sound characteristics and compare the snoring image characteristic with basic snoring image characteristics to select one of the snoring image characteristic in a same waveform, and provides the first angle control order and the second angle control order corresponding to the selected snoring image characteristic;

wherein the snoring image characteristic is classified according to the basic snoring sound characteristics and a plurality of basic snoring image characteristics for different respiratory actions.

4. The bed set of claim 3, wherein the image receiver further uses an adaptive partial averaging filter to enhance a noise ratio of the plurality of the respiratory image signals obtained from the user during the time period.

5. The bed set of claim 4, wherein the plurality of the respiratory image signals are a side view.

6. The bed set of claim 3, wherein the snoring image characteristics is the region ratio of respiratory tract and the interested area during a respiratory action.

7. The bed set of claim 6, wherein the respiratory area is obtained from the interested area divided by an Active Contour Model (ACM).

8. The bed set of claim 3, wherein the control processor further obtains a time reference according to a receiving sequence of the plurality of the respiratory image signals, and corrects a time error between snoring sound characteristic and snoring image characteristic based on the time reference.

9. The bed set of claim 1, wherein the sound receiver further filters a noise of the respiratory sound signal by Principal Component Analysis (PCA).

10. The bed set of claim 1, wherein the respiratory sound signal is a spectrum harmonic wave obtained by short-time Fourier transforming with a Gauss window function from the respiratory sound signal during a respiratory action.

11. The bed set of claim 1, wherein the first pillow and the second pillow incline the first angle and the second angle in the same direction, and a rotating axis of the first pillow and the second pillow is parallel to the body of the user.

12. The bed set of claim 1, wherein the first angle and second angle are respectively one of 15 degrees, 30 degrees and 60 degrees.

13. The bed set of claim 1, wherein the first pillow and the second pillow are a part of a L-shaped pillow.

* * * * *